United States Patent [19]

Hübner

[11] 4,111,034
[45] Sep. 5, 1978

[54] APPARATUS FOR MONITORING THE SOLVENT CONTENT OF AIR

[76] Inventor: Rolf H. Hübner, Pfarrer-Kneipp-Str. 9, Dortmund, Germany, 4600

[21] Appl. No.: 785,690

[22] Filed: Apr. 7, 1977

[30] Foreign Application Priority Data

Apr. 8, 1976 [DE] Fed. Rep. of Germany ....... 2615188

[51] Int. Cl.² ........................................... G01N 27/04
[52] U.S. Cl. ..................................... 73/23; 68/13 R; 68/18 R
[58] Field of Search ............... 73/23, 27 R; 23/254 E; 340/237 R; 68/13 R, 18 R

[56] References Cited

U.S. PATENT DOCUMENTS

| 3,388,567 | 6/1968 | Oles | 68/18 |
|---|---|---|---|
| 3,586,486 | 6/1971 | Kim et al. | 73/27 X |
| 3,877,291 | 4/1975 | Hoppesch et al. | 73/27 |
| 3,879,717 | 4/1975 | Gruensfelder | 340/237 |
| 3,901,067 | 8/1975 | Boardman et al. | 73/23 |
| 3,953,173 | 4/1976 | Obayashi et al. | 73/27 |
| 3,955,268 | 5/1976 | Chou et al. | 73/23 X |
| 4,028,057 | 6/1977 | Nelson | 23/254 |

Primary Examiner—Herbert Goldstein
Attorney, Agent, or Firm—Karl F. Ross

[57] ABSTRACT

An apparatus for monitoring the solvent content of air, especially for detecting the presence of perchloroethylene or trichloroethylene in association with a drycleaning plant, for measuring the concentration of the solvent and/or for triggering an alarm in the event a solvent concentration exceeds a predetermined limit. The sensor comprises a metal oxide semiconductor electrically heated to a predetermined temperature and having a surface exposed to the solvent molecules in the air so that its electrical resistance or conductivity changes as a function of the solvent concentration.

11 Claims, 6 Drawing Figures

APPARATUS FOR MONITORING THE SOLVENT CONTENT OF AIR

FIELD OF THE INVENTION

The present invention relates to an apparatus for monitoring the solvent content of air, especially in association with drycleaning and, more particularly, for measuring the concentration of perchloroethylene or trichloroethylene in air or detecting a level of such solvents above a predetermined limit.

BACKGROUND OF THE INVENTION

Perchloroethylene and trichloroethylene, two solvents commonly used in drycleaning, are highly toxic and hence the leakage of such solvents into the environment from a drycleaning plant may prove to be undesirable. In addition it is advantageous to detect the concentration of the solvent in the airstream used within the drycleaning machine or to establish the level of the solvent in air released from the drycleaning machine. To this end it has been found to be advantageous to monitor the level of perchloroethylene or trichloroethylene in association with a drycleaning plant.

The expression "monitoring the solvent content of the air" is used herein to refer to several alternatives. For example, it may involve determining whether the solvent content of the air exceeds a predetermined level. Alternatively, it may involve a measurement of the level of solvent content in the air. Finally, it may involve a determination as to whether or not the air contains traces of solvent. Each of these conditions and any combination thereof are referred to collectively as a monitoring of the solvent content.

To establish the solvent content of air, there have been two techniques which have been employed heretofore. In the first of these techniques, a sampling tube is used to quantitatively determine the solvent content of the air by a sampling technique which cannot be carried out continuously. In the second approach a halogen test lamp is used and is effective to establish whether or not the air contains solvent, but is not effective for a continuous determination of the level of the solvent in the air. Consequently, notwithstanding the fact that environmental protection laws require that solvent concentration in the region of a drycleaning plant be maintained below a certain level, there has been no effective way heretofore, to the knowledge of applicant, to provide a continuous monitoring of the solvent content of the air in all of the three respects mentioned previously.

OBJECT OF THE INVENTION

It is the object of the present invention to provide an apparatus for the continuous monitoring of air in association with drycleaning for the content of perchloroethylene or trichloroethylene, or other drycleaning solvent, so as to trigger an alarm upon the existing of a predetermined level and/or for controlling a process in response to the solvent level and/or for merely measuring the concentration of solvent in such air.

SUMMARY OF THE INVENTION

The apparatus of the present invention achieves the foregoing objects by providing a solvent detector which comprises a metal oxide semiconductor which is electrically heated to a temperature sufficient to enable the absorption of solvent molecules upon the surface to modify the conductivity or resistivity of the semiconductor and provide an electrical output representing the concentration of the concentration in the air in the region of the semiconductor's surface. This temperature, which depends upon the composition of the semiconductor, may be of the order of 30° to 300° C and the semiconductor may be a silicon dioxide semiconductor of any conventional design having the semiconductive surface exposed. Surprisingly, the presence of perchloralethylene or trichloroethylene solvent in the air contacting this semiconductor, when the latter is heated, as indicated, provides an electrical output, in terms of resistance or conductance which is a function of the concentration of the solvent in the air.

Preferably, the metal oxide semiconductor, or a plurality of metal oxide semiconductors, are disposed in a measuring chamber and is provided, upstream with respect to the flow of air through the measuring chamber, with a sintered-metal plate permeable to air and the solvent contained therein. The sintered-metal plate, according to the invention, protects the metal oxide semiconductor against contamination.

Advantageously, upstream of the metal oxide semiconductor, and upstream of the sintered-metal filter plate when one is provided, there is disposed a baffle plate or the like adapted to collect particles of moisture which may be entrained in the air stream by impingement-baffle principles.

In dry cleaning using a solvent such as perchloroethylene and/or trichloroethylene, there is customarily provided an apparatus in which the fabric to be treated is tumbled in a perforated drum, the solvent is admitted to the drum, the solvent is extracted by rotating the drum at high speed, and an air stream is blown through the drum to entrain the residual solvent from the fabric. The solvent may be collected from this air stream by a condenser and recycled to the dry cleaning operation before the air stream is brought into contact with an adsorber, such as an activated carbon filter, and released into the atmosphere. The activated carbon filter serves to remove traces of the solvent from the air stream.

Various jurisdictions have promulgated laws for the protection of the environment which have established certain limits for the maximum permissible concentration of such solvents in the air.

Such limits generally exist for the room air (maximum work place concentration), for the air discharged from the active carbon filter, and for the release of air from the work place into the environment.

The present invention provides, in the first instance, an apparatus for monitoring the solvent content of air in association with a dry-cleaning plant and, especially, a dry-cleaning plant with a closed solvent circulation path and/or with a waste-air discharge duct. According to the invention, the measuring unit, i.e. the measuring chamber, has at least one inlet for room air, at least one inlet for the monitoring of air which may contain leaked quantities of solvent, at least one inlet for air discharged from the plant, and/or at least one inlet connected to a sampling tube which can be flexible and can be moved from place to place and advantageously provided with a pump for drawing air through this flexible intake into the measuring chamber.

Conventional apparatus has been capable only of monitoring the solvent content of the room air with greater or lesser effectiveness for the reasons noted earlier. For this reason, in place of a monitoring of the solvent content of the discharged air, and hence the effectiveness of the active carbon filter, the dry cleaning apparatus has customarily been operated with other criteria. For example, the regeneration cycle for the active carbon filter is effected after a predetermined operating period independently of the ability of the filter to recover traces of solvent from the air. Naturally, this operating period must be less than the maximum duration required for saturation of the active carbon filter.

As a consequence, in many cases, for the sake of safety, the active carbon filter may be regenerated before it has been fully utilized, thereby decreasing the useful life of the adsorbent and complicating the operation of the dry cleaning unit.

With the system of the present invention, however, which permits direct monitoring of the solvent content of the discharged air, it is possible to switch over to regeneration of the active carbon filter only when an increased concentration of solvent in the discharged air is observed or upon the detection of solvent in the discharged air, so as to prevent premature regeneration of the active carbon filter and thereby improve the utilization thereof.

According to the invention, the apparatus is also suitable for monitoring leakage from the apparatus and, to this end, the closed solvent cycle (recirculation path) is sparged with air (so-called leakage-monitoring air) and the leakage monitoring air is fed through the measuring chamber of the apparatus of the invention so that the presence of a substantial proportion of solvent in this air can indicate that a leak has occurred.

It is also possible with the present invention to detect the location of a leak using the flexible air pickup device and pump, the pickup unit being moved from place to place along the solvent recirculation path.

According to the invention, a pump can be provided ahead of one of the aforementioned inlets or each such inlet may be provided with a respective pump so that one or another of the aforementioned air streams can be fed continuously through the measuring chamber and monitored for solvent concentration.

A pump need not be provided in the discharge duct of the machine when a pressure differential is created therein, in accordance with the present invention, by providing a throttle along the air path and connecting the inlet to the high pressure side of the throttle while the outlet of the measuring chamber is connected to the low pressure side thereof. In this case, a portion of the air to be discharged is continuously circulated through the measuring chamber.

According to a further feature of the invention, the detecting means or indicator is provided with at least one setpoint value generator, which is preferably adjustable, at least one comparator receiving an actual value signal from the detector and the setpoint signal, and at least one alone and/or control unit and/or indicator unit. With this construction, when the actual value exceeds the setpoint value, the comparator generates a signal which can trigger the alarm and/or a control unit for example to set into operation the adsorver-generating process. The indicator can be connected ahead of the comparator to generate a continuous visual indication (measurement) of the solvent concentration.

Advantageously, the measuring chamber is provided with first inlet for delivering room air to the measuring chamber, a second inlet for delivering leak-monitoring air thereto and a third inlet communicating with the duct for discharging the air from the dry cleaning machine into the atmosphere downstream of the carbon filter. The measuring unit can be provided with a solvent indicator responsive to room air, a solvent indicator responsive to leak monitoring air and a solvent indicator responsive to the solvent concentration in the air discharged from the dry cleaning machine. Furthermore, three separate setpoint value generators can be provided and three comparators, each receiving one setpoint value and a respective actual value. The comparators can operate respective alarm generators or control generators for appropriate modification of the dry cleaning machine.

However, since the concentration of solvent in the work place air does not change rapidly, the expense involved in a complete three-channel apparatus of the aforedescribed type can be avoided. In this case, only a single solvent indicator, three setpoint generators, a single comparator and preferably three alarm transmitters and/or control transmitters are provided. In addition, a switchover device is employed for commutating the room air supply with the appropriate setpoint generator and alarm transmitter, and each of the other inlets with the respective setpoint generator and alarm transmitter or control transmitter.

Preferably the system is switched over automatically at predetermined time intervals from room air monitoring to leakage air monitoring to discharge air monitoring.

BRIEF DESCRIPTION OF THE DRAWING

The above and other objects, features and advantages of the present invention will become more readily apparent from the following description, reference being made to the accompanying schematic drawing in which.

SPECIFIC DESCRIPTION

Figure 6:
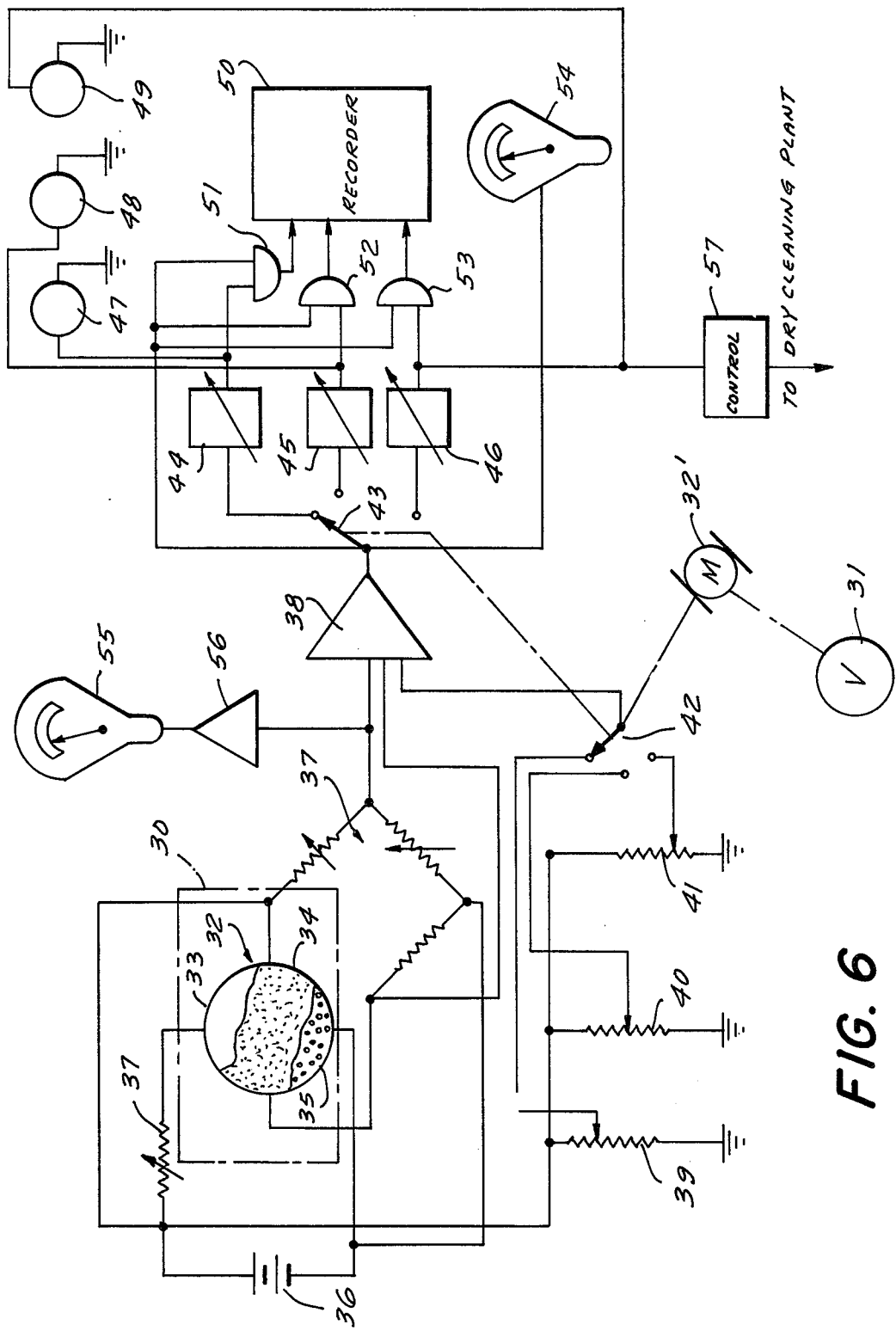
FIG. 6 is a circuit diagram illustrating principles of the present invention.

Referring first to FIG. 6 of the drawing, from which the principles of the present invention will become apparent more quickly, it will be evident that the apparatus comprises a measuring chamber represented diagrammatically in dot-dash lines at 30 to which the air to be monitored is fed under the control of a valve arrangement, e.g. represented at 31. The valve system 31 is driven by a motor 32 to periodically sample room air, leakage air and discharge air from a dry cleaning apparatus.

The sensor 32 comprises a substrate 33 formed with a metal oxide semiconductive layer 34 and covered by a sintered-metal filter plate 35 which prevents contamination of the semiconductor 34, the latter being heated by passing an electric current through the substrate 33 from a battery 36 under the control of a resistor 37 to establish the necessary operating temperature as previously described. The resistance of the semiconductor 34 varies as a function of the solvent concentration and hence the semiconductor is connected in a wheatstone bridge 37 which is energized via the battery 36 and has its output terminals connected to a comparator 38 which compares the input from the bridge with a setpoint value delivered by one of the three reference value or setpoint value generators 39, 40, 41. These setpoint value generators are represented as variable resistors connected in voltage divider configurations and having respective voltages tapped therefrom. For example, the setpoint-value generator 39 may produce the setpoint representing the maximum permissible concentration of room air, the setpoint generator 40 may generate a voltage value representing a limit beyond which leakage is significant requiring correction, and the setpoint generator 41 may produce an outpoint representing a value of solvent concentration in the discharge air necessary to initiate the regeneration cycle.

The outputs of the setpoint value generator 39 through 41 are commutated by a commutating switch 42 to the setpoint terminal of the comparator 38.

A switch 43 ganged with switch 42 is provided between the output of the comparator 38 and respective Schmitt-trigger circuits 44 through 46, the outputs of which trigger alarms 47 through 49, respectively. In addition, it may be desirable to record the occurrence of a level of the solvent concentration for each of the values in the event they exceed the maximum permissible limits. For this purpose a three-point recorder 50 is provided, the inputs to the recorders being applied through AND-gates 51 through 53, the latter receiving inputs from the threshold trigger circuits 44-46 and an input from the output of the comparator 38.

In addition, an indicator 54, e.g. a meter, may register the output of comparator 38 to indicate, via a needle on an appropriate scale, the degree to which a particular concentration exceeds the maximum permissible value thereof. A further indicator 55 may be connected via an amplifier 56 to the output of the bridge 37 to provide a constant indication of the concentration of the solvent detected.

The Schmitt-trigger 46 is also connected to a control circuit 57 for initiating regeneration of the active carbon adsorber.

The circuit operates in the manner described generally above in that the bridge commutates the respective setpoint value generated to the comparator 38 to apply the appropriate setpoint value which is compared with the actual value delivered by the bridge 37. The output of the comparator 38 is applied simultaneously to the respective threshold trigger 44 through 46 which operates the respective alarm 47 through 49 in the event the actual value of the concentration exceeds the setpoint value by a predetermined limit. The concentrations are recorded as will be apparent at 50 and are indicated on meters 54 and 55 as described.

In FIGS. 1 through 5 there is illustrated an apparatus for monitoring the solvent concentration of air, especially for the monitoring of the concentration of perchloroethylene or trichloroethylene in air associated with a dry cleaning apparatus. The system consists basically of a measuring unit 1 with a solvent level indicator 2 and an evaluating unit 3 connected to the measuring unit 1.

The solvent detector 2 of the measuring unit 1 of the apparatus according to the invention comprises a metal oxide semiconductor as described which is electrically heated to a predetermined temperature and whose surface can be contacted with solvent molecules and trained by the air stream which is monitored. The output of the metal oxide semiconductor 4, in terms of electrical conductivity or resistivity, is a function of the solvent concentration of the air and hence the rated resolvent molecules tend to adsorb upon the surface of the semiconductor.

The metal oxide semiconductor 4 is disposed in a measuring chamber 5 and is shielded by a sintered metal plate 6 permeable to air and the entrained solvent molecules. A baffle plate 7 is disposed ahead of the sintered metal plate 6 to deflect droplets of solvent or moisture which may be entrained in the air stream.

Figure 1:
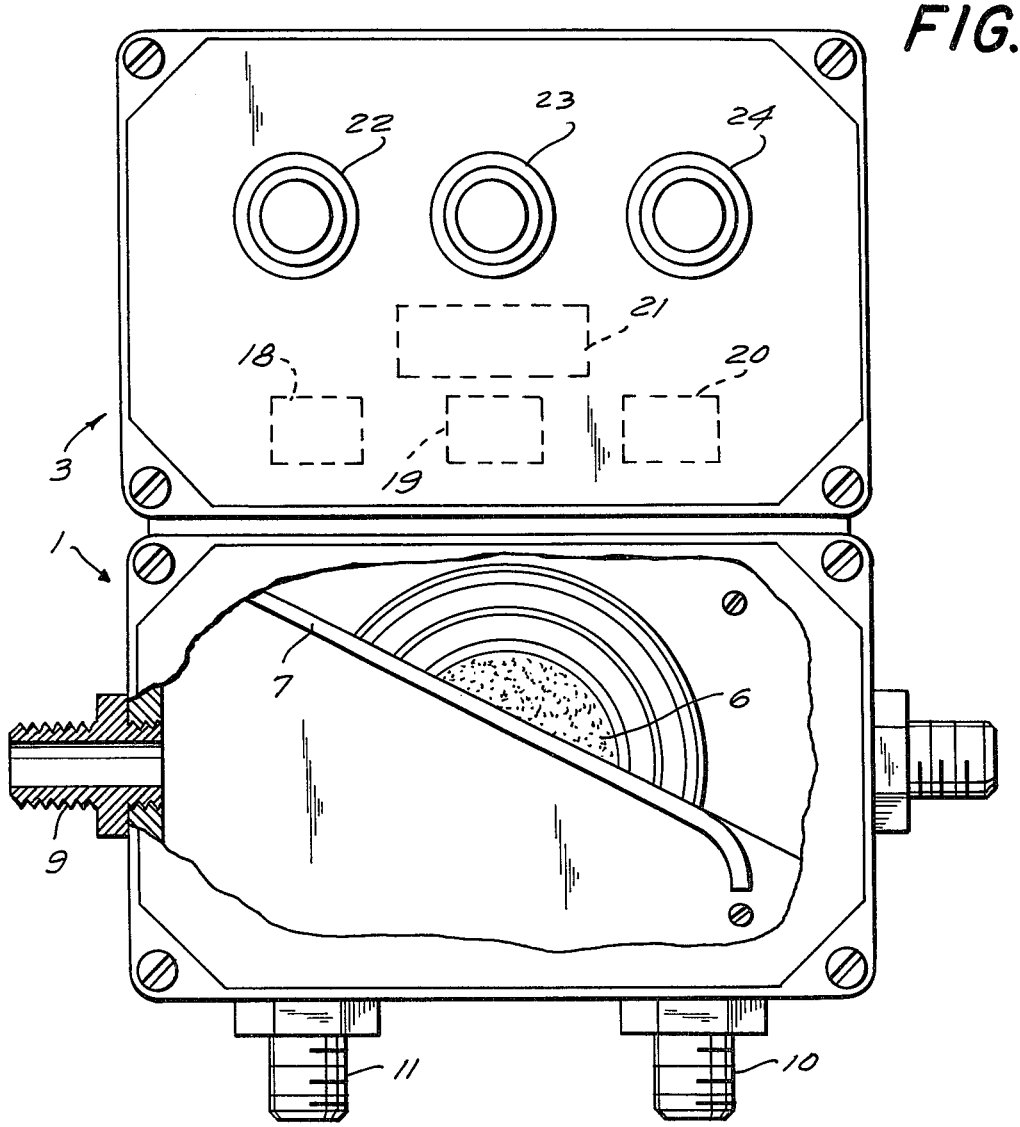
FIG. 1 is a front-elevational view of an apparatus according to the invention for monitoring the solvent concentration of air, partly in section.
Figure 2:
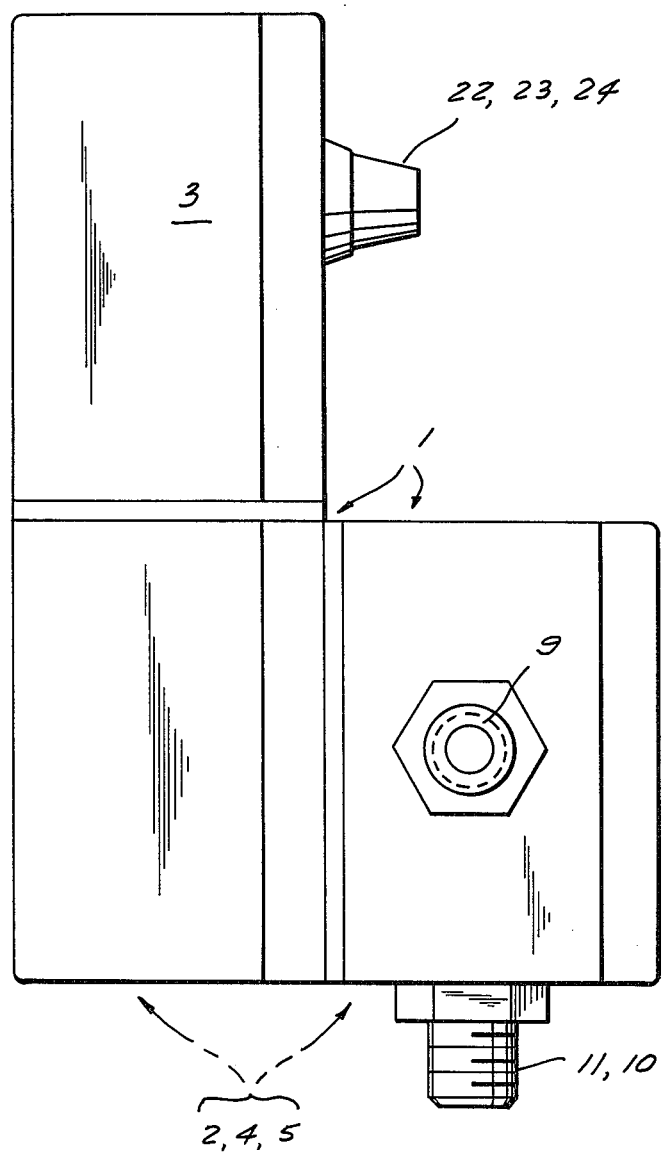
FIG. 2 is a side-elevational view of the apparatus of FIG. 1.

The apparatus of FIGS. 1 and 2, as has previously been indicated, serves to monitor the solvent content in association with a dry cleaning apparatus not shown. The latter can have a closed solvent circulation path and a plurality of active carbon filters which are switched into effective condition and are regenerated via the control circuit previously described. The apparatus does have a discharge duct 8 traversed by the air which is to be released into the atmosphere and downstream of the active carbon filter or filters.

Figure 3:
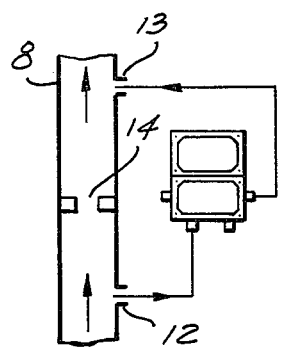
FIGS. 3 through 5 are views showing different operating modes of the apparatus illustrated in FIGS. 1 and 2.
Figures 4, 5:
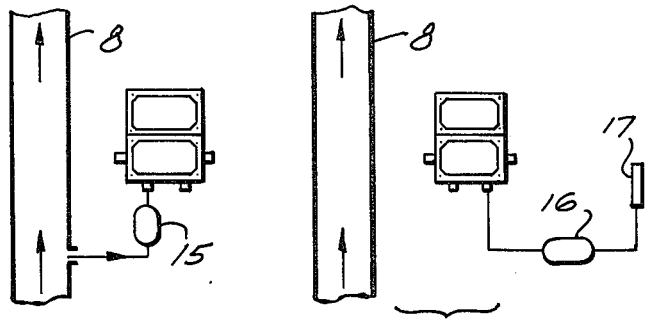

As can be seen in FIGS. 3 and 4, the solvent content of the air discharged through the duct 8 can be measured by providing this duct with a throttle 14 so that a pressure differential is created between upstream and downstream sides of the duct 8 which are connected at 12 and 13 to an inlet and an outlet of the measuring chamber.

According to the invention, the measuring chamber has a room air inlet 9, a leakage air inlet 10 and a discharge air inlet 11. In the embodiment of FIG. 3, the discharge inlet is connected at 12 to the duct 8 while an outlet of the measuring chamber is connected at 13 upstream of the constriction or throttle 14. The pressure differential causes the circulation of discharge air through the measuring chamber.

In FIG. 4 I have shown a mode of operation where only a gas connection, e.g. the connection 12, to the duct 8 is connected to the measuring chamber through a suction pump 15. This system can be used as an alternative to that of FIG. 3. Furthermore, this arrangement can be employed to detect leaks within the apparatus of the solvent.

As can be seen in FIG. 5, a flexible pipe provided with a suction head 17 can be provided for the measuring chamber to scan the apparatus for leaks and to permit the pump 16 to draw leakage air from any location in the apparatus into the measuring chamber. A further pump can be connected at the inlet 9 to supply air from the ambient atmosphere.

The fittings 9 through 11 can be connected to the several sources of solvent-containing air via the valve 31 previously described.

The evaluating unit 3 of the apparatus can comprise, as has been illustrated only diagrammatically in FIGS. 1 and 2, three setpoint value generators 18, 19 and 20 which feed into a common comparator 21 which also receives the input from the sensor. The comparator 21 operates, as described, three alarm units 22, 23 and 24 and control units where necessary. A switchover device is provided in this apparatus as described at 42, 43 in FIG. 6.

The apparatus of FIGS. 1 through 5 thus is capable of measuring the concentration of solvent in the room air through the fitting 9, the associated setpoint value generator 8, and appropriate threshold circuitry as described to trigger the alarm 22 when the concentration of solvent in the air is excessive. Similarly, the setpoint generators 19 and 20 are effective when the fittings 10 and 11 are operative to trigger respective alarms 23 and 24 in the event the respective thresholds are exceeded. In this embodiment as in the embodiment of FIG. 6, the motor 32' operates the switching or commutating unit periodically to carry out room air monitoring, leakage air monitoring and discharge air monitoring in succession and at predetermined intervals.

I claim:

1. An apparatus for monitoring of the solvent content of air in association with a dry cleaning plant, said apparatus comprising:

at least one metal oxide semiconductor responsive to the concentration of solvent in air to be monitored and disposed in a measuring chamber adapted to successively receive solvent-containing air from a plurality of sources;

circuit means connected to said semiconductor for indicating the concentration detected by said semiconductor;

means for electrically heating said semiconductor to a predetermined temperature;

a respective setpoint value generator assigned to each of said sources;

a comparator means for sequentially and periodically connecting each of setpoint value generators to said comparator in accordance with the source supplying air to said chamber, said comparator having an output; and respective indicators sequentially supplied with said output by said commutator means.

2. The apparatus defined in claim 1 wherein said sources include at least one air inlet, said apparatus further comprising a sintered metal permeable to air and solvent molecules entrained therewith and disposed between said semiconductor and said inlet for protecting said semiconductor against contamination.

3. The apparatus defined in claim 2, further comprising a baffle plate between said semiconductor and said inlet for intercepting droplets entrained with said air.

4. The apparatus defined in claim 1 wherein said measuring chamber is provided with a first inlet for room air, a second inlet for leakage air and a third inlet for air discharged from said dry cleaning plant.

5. The apparatus defined in claim 4 wherein at least one of said inlets is connected to a flexible suction line provided with a pump.

6. The apparatus defined in claim 4, further comprising pump means connected to said measuring chamber for inducing air to flow into and through said chamber through at least one of said inlets.

7. The apparatus defined in claim 1 wherein said indicators include an alarm.

8. The apparatus defined in claim 1 wherein said indicator cooperate with a control unit for said dry cleaning plant.

9. The apparatus defined in claim 1 wherein said indicators include a meter providing a direct indication of the solvent concentration of the air contacting said semiconductor.

10. The apparatus defined in claim 1 wherein said commutator means is operated periodically.

11. The apparatus defined in claim 1 wherein said indicator means includes at least one alarm signalling device, at least one concentration measuring device, and at least one control device for operating said dry cleaning plant.

* * * * *